(12) United States Patent  
Rhodes et al.

(10) Patent No.: US 9,146,206 B2  
(45) Date of Patent: Sep. 29, 2015

(54) CAPACITANCE-BASED MOISTURE SENSOR

(75) Inventors: Michael L. Rhodes, Richfield, MN (US); Clayton S. Morton, Elkton, MD (US); James A. Chambers, Hawthorn Wds, IL (US); Graeme L. Jarvis, Marblehead, MA (US); Larry L. Hendrickson, Savoy, IL (US)

(73) Assignee: DEERE & COMPANY, Moline, IL (US)

( * ) Notice: Subject to any disclaimer, the term of this patent is extended or adjusted under 35 U.S.C. 154(b) by 661 days.

(21) Appl. No.: 13/365,388

(22) Filed: Feb. 3, 2012

(65) Prior Publication Data

US 2013/0200905 A1 Aug. 8, 2013

(51) Int. Cl.
*G01R 27/26* (2006.01)
*G01N 27/22* (2006.01)
*G01N 33/24* (2006.01)

(52) U.S. Cl.
CPC ............ *G01N 27/223* (2013.01); *G01N 33/246* (2013.01)

(58) Field of Classification Search
None
See application file for complete search history.

(56) References Cited

U.S. PATENT DOCUMENTS

| | | | |
|---|---|---|---|
| 2,555,977 A | 6/1951 | Kline | |
| 2,724,798 A | 11/1955 | Hare et al. | |
| 3,771,548 A | 11/1973 | Rauchwerger | |
| 4,540,936 A | 9/1985 | Walsh | |
| 5,260,666 A | 11/1993 | Dishman et al. | |
| 5,418,466 A | 5/1995 | Watson et al. | |
| 5,479,104 A | 12/1995 | Cambell | |
| 7,042,234 B2 | 5/2006 | Buss | |
| 7,150,184 B1 * | 12/2006 | Scott et al. | ........................ 73/73 |
| 7,240,743 B2 | 7/2007 | Buss et al. | |
| 7,535,237 B1 | 5/2009 | Campbell | |

OTHER PUBLICATIONS

Robichaud P.R. et al. "Measuring duff moisture content in the field using a portable meter sensitive to a dielectric permittivity", International Journal of Wildland Fire, vol. 13, No. 3, Nov. 16, 2004, pp. 343-353, DOI: http//dx.doi.org/10.1071/WF03072 (11 pages).
Office Action from European Patent Office in counterpart EP Application No. 13153427.3 (6 pages), May 2, 2013.

* cited by examiner

*Primary Examiner* — Melissa Koval
*Assistant Examiner* — Stephen G Armstrong

(57) ABSTRACT

A capacitance-based moisture sensor may include a sleeve having an internal cavity, a container filled with soil or other material inserted into the internal cavity, and a pair of ring-shaped conductive bands around the exterior of the sleeve forming a capacitor and providing a frequency output. The rings positioned around a perimeter of the sleeve may be connected to a fixed inductor to form an oscillator with a variable frequency output. The sensor may be calibrated from the frequency output for each of a plurality of substances, measuring the volumetric water content for saturation of the material, and determining at least one fitting constant in an equation wherein volumetric water content is a function of the frequency output and a plurality of fitting constants.

5 Claims, 2 Drawing Sheets

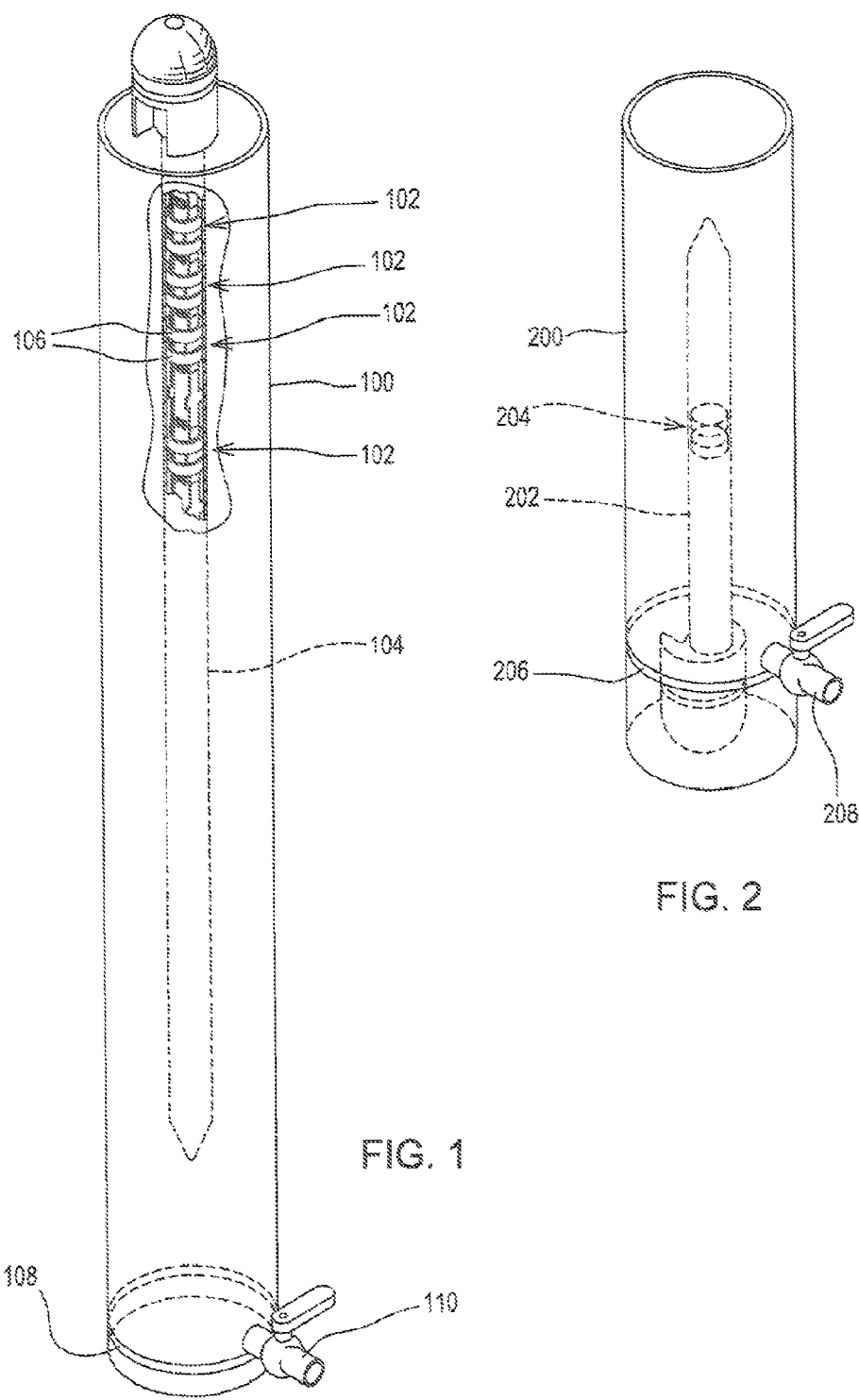

ically to capacitance-based
moisture sensors.

CAPACITANCE-BASED MOISTURE SENSOR

FIELD OF THE INVENTION

This invention relates generally to moisture sensing of soil or other materials, and more specifically to capacitance-based moisture sensors.

BACKGROUND OF THE INVENTION

Volumetric water content of soil or other materials may be measured using a probe having one or more capacitance-based moisture sensors. Each capacitance-based moisture sensor may include two conductive rings spaced by a dielectric to form a capacitor. The sensors may be arranged and fastened inside a probe which may be a plastic access tube that may be inserted in the soil. The electric field of each capacitor extends beyond the access tube and interacts with the soil around the tube to make the value of the capacitor variable. The variable capacitor may be coupled with a fixed inductor to form a free running oscillator with a frequency $F=1/(2\pi\sqrt{LC})$.

An example of such a device is shown in U.S. Pat. No. 5,418,466 entitled "Moisture and Salinity Sensor and Method of Use" relating to moisture and salinity measurement and in particular to a sensor and its method of use which may provide values for the moisture/complex dielectric constant of a variety of mediums. A sensor apparatus is arranged for indicating the complex dielectric constant and conductivity of a medium and uses a tuned circuit. The tuned circuit oscillates such that the frequency of oscillation is representative of the complex dielectric constant of the medium.

Capacitance-based moisture sensors must be calibrated. Calibration needs to be done for each different sensor design and soil type. Calibration may be accomplished by measuring the frequency response of a representative sensor to a specified soil at several different volumetric water contents. The calibration process may involve installing one or more sensor assemblies in an open field of a specified soil type and monitoring the sensor response as water is added to the soil. The process may require stabilizing the soil for several days or weeks before each of the soil samples may be physically removed and analyzed to establish a fitted response curve to the soil readings. At each of the various moisture contents, the soil may be removed and sectioned with earth moving equipment to obtain a physical soil sample for volumetric analysis. This calibration process may be time and labor intensive. A more efficient and cost effective calibration apparatus and method is needed for capacitance-based moisture sensors for soil or other materials.

Migration mediums have been proposed for use with capacitance-based moisture sensors in an effort to reduce or eliminate calibration requirements. For example, U.S. Pat. No. 7,042,234 entitled "Soil Matric Potential and Salinity Measurement Apparatus and Method of Use" relates to a soil measurement arrangement that includes a capacitive based soil moisture and salinity sensor, a predetermined moisture migration medium located in a volume adjacent said sensor so that the medium substantially occupies the field of influence of said sensor. The medium is in moisture communication with the soil to be measured, and said sensor is adapted to measure and produce data representative of the volumetric water content of said medium. A sensor data processing means determines both the soil moisture and salinity of said medium. By using the measured volumetric soil moisture content and the moisture release curve of the medium, it is possible to derive the matric potential of the soil. The measured salinity of the medium corresponds to the salinity of the soil that is in moisture communication with the medium. However, a migration medium may increases the hole diameter for in-ground installation of the sensor and requires additional time and cost.

There is a need for a small capacitance-based moisture sensor and method for testing and characterizing soil types that is cost-efficient. There also is a need for an apparatus and method for calibration of capacitance-based moisture sensors that is small, cost-efficient, fast to operate and less labor intensive.

SUMMARY OF THE INVENTION

A capacitance-based moisture sensor that is smaller, faster and/or less labor intensive. In one embodiment, the sensor may include a sleeve having an internal cavity, a container filled with soil or other material inserted into the internal cavity, and a pair of ring-shaped conductive bands around the exterior of the sleeve forming a capacitor and providing a frequency output. The rings positioned around a perimeter of the sleeve may be connected to a fixed inductor to form an oscillator with a variable frequency output. Additionally, a calibration method for a capacitance-base moisture sensor may use the sleeve or a calibration fixture. The sensor may be calibrated from the frequency output for each of a plurality of substances, measuring the volumetric water content for saturation of the material, and determining at least one fitting constant in an equation wherein volumetric water content is a function of the frequency output and a plurality of fitting constants.

BRIEF DESCRIPTION OF THE DRAWINGS

FIG. 1 is a side perspective view of a calibration fixture with a capacitance-based moisture sensor according to one embodiment of the invention.

FIG. 2 is a side perspective view of a calibration fixture with a capacitance-based moisture sensor according to a second embodiment of the invention.

DESCRIPTION OF THE PREFERRED EMBODIMENT

Figure 3:
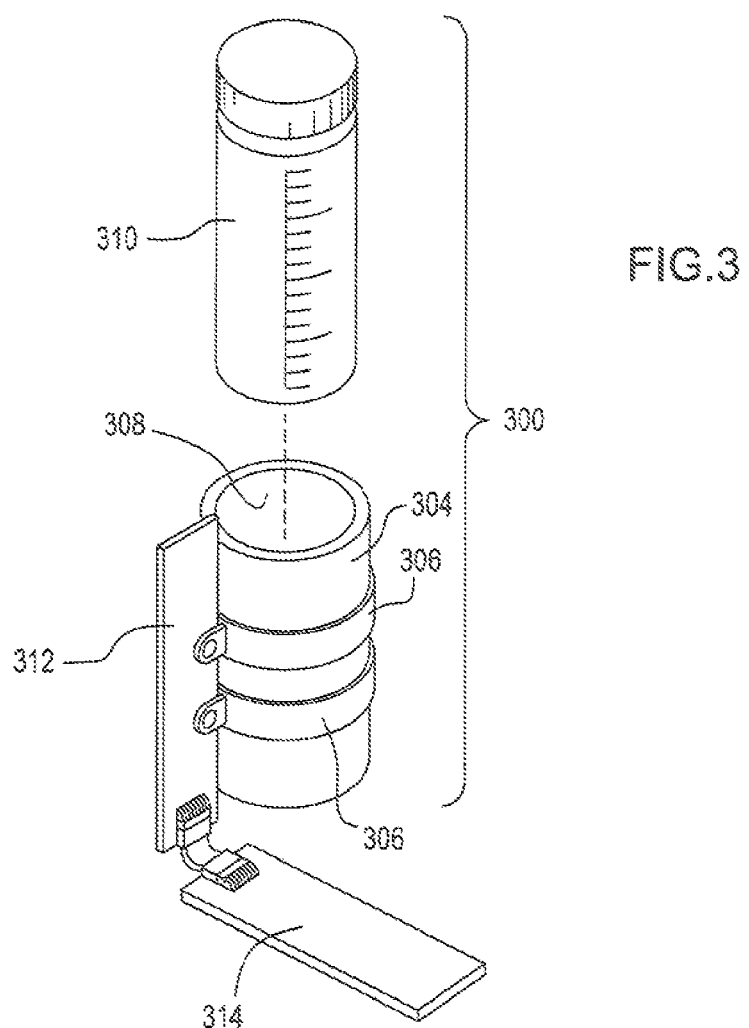
FIG. 3 is a side perspective view of a capacitance-based moisture sensor according to a third embodiment of the invention.

FIG. 1 shows a first embodiment of calibration fixture 100 to calibrate one or more capacitance-based moisture sensors 102 for a soil type. Calibration fixture 100 may be a housing having a known volume larger than probe 104. For example, calibration fixture 100 may be a PVC pipe having a volume of about 2 liters, and a diameter of about 4 inches to about 8 inches. The calibration fixture may be cylindrical or non-cylindrical, and may have a width greater than the sphere of influence of the capacitance-based moisture sensor(s) 102 that are calibrated in the fixture.

In one embodiment, each capacitance-based moisture sensor 102 may include a pair of conductive rings spaced by a dielectric to form a capacitor, and may be arranged and fastened to a carrier inside probe 104. The carrier also may include an oscillator board. The probe may be a plastic pipe having an internal diameter of about two inches and a wall thickness of about 3/16 inches. Each sensor may be positioned in direct contact with the inside of the probe wall. For example, each sensor 102 may include a pair of copper bands 106, each band having a diameter of about 2 inches, and a width of about ½ inch. The copper bands may be spaced in an axial direction from each other by about ½ inch. The electric field of the capacitor may extend beyond the probe wall and may interact with the soil or other substance around the probe to make the value of the capacitor variable. The variable capacitor may be coupled with a fixed inductor (L) to form a free running oscillator with a frequency $F=1/(2\pi\sqrt{LC})$.

In the embodiment of FIG. 1, bottom seal 108 may be provided at the bottom surface of calibration fixture 100. Optionally, a layer of sand also may be provided immediately above the bottom seal. Additionally, drain cock 110 may be located in the wall of the calibration fixture adjacent the bottom seal and may be used to drain or remove water from the calibration fixture.

In the embodiment of FIG. 1, calibration of capacitance-based moisture sensor 102 for a particular soil type may include inserting probe 104 with at least one sensor into the calibration fixture. Sensor frequency output may be obtained for each of several substances including air, water, dry matrix and saturated soil introduced into the calibration fixture.

In the embodiment of FIG. 1, calibration fixture 100 may have a volume of 2 liters. Sensor frequency output may be obtained from sensor 102 with only air in the calibration fixture, and with only water in the calibration fixture. A known volume of dry matrix of a selected soil type may be introduced into the calibration fixture, and sensor frequency output may be obtained for the dry matrix. The soil may be compacted to a known compaction pressure.

In one embodiment, the sensor calibration method may include introducing a known volume of water into the calibration fixture until the soil is completely saturated. The method also may include measuring the volume of water, and determining the volumetric fraction of water, or $W_v$, added to the calibration fixture to saturate the dry matrix of the selected soil type. For example, if the volume of water added to saturate the dry matrix in the 2 liter calibration fixture was 807 ml, the volumetric water content is 0.807/2, or $W_v=0.4035$. Sensor frequency output may be obtained for the saturated soil. Optionally, drain cock 110 then may be opened so that water may drain by gravity out of the fixture, and the volume of drained water may be measured.

In one embodiment, the sensor calibration method may include converting each sensor frequency reading, such as frequencies in the range of 100 MHz to 200 MHz, to a scaled frequency value. The highest sensor frequency reading is for air (for example, 161 Mhz) and may be converted to a minimum scaled frequency value of 0.000. The lowest sensor frequency reading is for water (for example, 115 MHz) and may be converted to a maximum scaled frequency value of 1.000. Each of the other sensor frequency readings may be converted to a scaled frequency value between 0.000 and 1.000 by linear interpolation. For example, a sensor frequency reading of 129 MHz for dry matrix may be converted to a scaled frequency value of 0.695, and a sensor frequency reading of 119 MHz for saturated soil may be converted to a scaled frequency value of 0.906. Each scaled frequency value also may be referred to as the normalized response (NR).

In one embodiment, the sensor calibration method may include solving an equation wherein volumetric water content is a function of the sensor frequency response or scaled frequency value for saturated soil, along with one or more fitting constants. For example, one such equation is $W_v=((NR-C)/A)^{(1/B)}$ and may be solved for one or more fitting constants A, B or C. In this example, $W_v$ is the volumetric fraction of water added to the calibration fixture to saturate the dry matrix, NR is the normalized response for the saturated soil, and A, B and C are fitting constants. In this example, fitting constant B may be based on generalized refractive dielectric models for moist soils at frequencies in a desired range of 100 MHz to 200 MHz. For example, an appropriate value for fitting constant B is 0.450 for most soils in a sensor frequency range of 100 MHz to 200 MHz. Additionally, fitting constant C may be based on the sensor's scaled frequency value for dry matrix of the selected soil type. In this example, C=0.695. The equation then may be solved for fitting constant A which is the remaining value. In this example, A =0.040.

In one embodiment, after the method and apparatus of FIG. 1 is used to determine fitting constants A, B and C for a particular sensor and soil type, the same equation and the same values for fitting constants may be applied to reliably and repeatably determine volumetric water content from the sensor's frequency response for that sensor and soil type.

FIG. 2 shows a second embodiment of sensor calibration fixture 200 in which probe 202 is in an inverted position. Capacitance-based moisture sensor 204 may be mounted to the internal surface of the probe in direct contact with the inside probe wall. Bottom seal 206 may be provided at or near the bottom surface of calibration fixture 200, and drain cock 208 may be used to drain or remove water from the calibration fixture. The method for the calibration apparatus of FIG. 2 may be substantially the same as for the apparatus of FIG. 1.

FIG. 3 shows an embodiment of capacitance-based moisture sensor 300 that may be used for testing of soil or other materials for moisture content, characterizing soil types, and/or calibration of sensors for a selected soil type. Sensor 300 may be referred to as an internal sensor because soil or other material may be placed in a container or vessel 310 that is inserted inside a pair of ring-shaped conductive bands 306. The pair of ring-shaped conductive bands 306 form a fringing capacitor positioned around the exterior of hollow cylinder or sleeve 304.

Capacitance-based moisture sensor 300 shown in FIG. 3 may be used to calibrate sensors having the same or substantially the same capacitor dimensions and inductor characteristics. For example, calibration using the apparatus of FIG. 3 may provide the same or substantially the same results as the apparatus of FIG. 1 or FIG. 2. In FIG. 3, ring-shaped conductive bands 306 may be coupled to the same or similar fixed inductor or oscillator board to form a free running oscillator having the same frequency output and range as those of FIGS. 1 and 2. As a result, calibration values obtained from sensor 300 are valid and may be used for capacitance-based moisture sensors mounted in a probe for insertion in soil. Sensor 300 may be significantly smaller in size, faster to operate and less labor intensive than other calibration devices and methods.

In the embodiment of FIG. 3, conductive bands 306 may form a fringing capacitor with each band having a preferred diameter of about 2 inches, and a preferred width of between about ½ inch and about 1 inch. The bands may be copper and may be spaced in an axial direction from each other by about ½ inch. The capacitor dimensions may be the same or substantially similar to capacitors in the capacitance-based moisture sensors shown in the probes of FIGS. 1 and 2. The electric field of the capacitor may extend through the wall of cylinder or sleeve 304 and interact with the substance in container 310 to make the value of the capacitor variable. The variable capacitor may be coupled with a fixed inductor (L) on oscillator board 312 to form a free running oscillator with a frequency $F=1/(2\pi\sqrt{LC})$. The oscillator board may be connected to microprocessor board 314 which may provide a frequency counter.

In the embodiment of FIG. 3, cylinder or sleeve 304 may be a one-piece plastic body having an outer diameter of about 2 inches and a length of between about 3 inches and about 6 inches. Cavity or internal passage 308 may extend at least partially or completely through the sleeve and may have an internal diameter of about 1.75 inches. Container 310 may be a glass or plastic jar dimensioned for insertion into the cavity or passage through the sleeve. The outer circumference of container 310 may be the same or slightly smaller than the internal circumference of sleeve 304 so that it has a snug but not tight fit. For example, the volume of the container may be about 250 ml.

In the embodiment of FIG. 3, calibration using sensor 300 for a particular soil or other material may include inserting container 310 into the cavity or internal passage 308 and obtaining sensor frequency output for each of several substances in the container. Sensor frequency output may be obtained with only air in the container, and with only water in the container. A known volume of dry matrix of the soil or other material may be introduced into the container, and sensor output may be obtained for the dry matrix.

In the embodiment of FIG. 3, water may be added into container 310 until the soil or other material is completely saturated. The volume of water added to the container may be measured, and the volumetric water content $W_v$ may be determined to saturate the dry matrix of the soil or other material. For example, if the volume of water added to saturate the dry matrix in the container was 101 ml, the volumetric water content is 101/250, or $W_v=0.404$. Sensor frequency output may be obtained for the saturated soil or other material.

In the embodiment of FIG. 3, the sensor calibration method may include converting each sensor frequency reading to a scaled frequency value, using the same method as describe for the embodiments of FIGS. 1 and 2.

In one embodiment, the sensor calibration method using the apparatus of FIG. 3 also may include solving an equation where volumetric water content is a function of the sensor frequency response or scaled frequency value for the saturated soil or other material, along with one or more fitting constants. For example, the equation $W_v=((NR-C)/A)^{(1/B)}$ may be solved for one or more fitting constants A, B or C. In the above equation, $W_v$ is the volumetric fraction of water added to the container to saturate the dry matrix, NR is the normalized response for the saturated soil or other material, and A, B and C are fitting constants. One or more other fitting constants may be included to compensate if there is any slight effect of the walls of container 310. In the above equation, fitting constant B may be based on generalized refractive dielectric models for moist soils at sensor frequencies in the desired range. For example, fitting constant B may be selected as 0.450 for a sensor frequency range of 100 MHz to 200 MHz. Additionally, fitting constant C may be based on the sensor's scaled frequency reading for the dry matrix for the soil or other material. In this example, C=0.695. The equation then may be solved for fitting constant A which is the only remaining unknown value. In this example, A=0.040. Once fitting constants A, B and C are determined for a particular sensor and soil or other material type, the above equation may be used to determine volumetric water content based on the sensor's frequency response for that soil or other material.

In one embodiment, the apparatus and method of FIG. 3 may be used to determine one or more fitting constants for a particular sensor and soil or other material, and the same fitting constants then may be used to reliably and repeatably determine volumetric water content from the sensor's frequency response for that soil or other material. Thus, the apparatus and method of FIG. 3 enables calibration of capacitance-based moisture sensors using a small sample in a container, instead of inserting a probe with a sensor in the ground.

In one embodiment, the capacitance-based moisture sensor of FIG. 3 may be used to measure moisture content of materials other than soil, including but not limited to agricultural products. Sensor 300 may be calibrated for a selected material using the apparatus and method described above. Sensor frequency may be obtained for dry material placed in the container and inserted into sleeve 304, and for the material after saturation with a measured volume of water. Fitting constants may be determined for that material and sensor using the same or similar equation described above. After calibration, the sensor may be used to reliably and repeatably measure moisture content of that material.

In one embodiment, the capacitance-based moisture sensor of FIG. 3 and the corresponding method may be used to characterize soils or other materials. For example, frequency output of sensor 300, for a dry matrix and/or saturated sample of an unknown soil, may be compared to the sensor's frequency output for one or more known soil types. The frequency output from sensor 300 may be the same or substantially similar as a known soil type such as sand, sandy loam, loam or clay.

Having described the preferred embodiment, it will become apparent that various modifications can be made without departing from the scope of the invention as defined in the accompanying claims.

We claim:

1. A capacitance-based moisture sensing method, comprising:
    filling a container having a known volume with a material;
    inserting the container into a hollow sleeve;
    obtaining a frequency output from a pair of ring-shaped conductive rings positioned around a perimeter of the sleeve and connected to a fixed inductor to form an oscillator with a variable frequency output; and
    determining a fitting constant A, B or C in an equation $W_v=((NR-C)/A)^{(1/B)}$ where $W_v$ is a volumetric water content of the material in the container and NR is a normalized value for the frequency output.

2. A capacitance-based moisture sensor calibration method, comprising:
    obtaining a frequency output from a capacitive-based moisture sensor for each of a plurality of substances including but not limited to air, water, dry matrix and saturated material;
    measuring the volumetric water content for saturation of the material; and
    determining at least one fitting constant in an equation wherein volumetric water content is a function of the frequency output and a plurality of fitting constants.

3. The capacitance-based moisture sensor calibration method of claim 2 further comprising inserting a probe carrying the capacitive-based moisture sensor into a calibration fixture larger in diameter than the probe, and placing each of the plurality of substances into the calibration fixture.

4. The capacitance-based moisture sensor calibration method of claim 2 further comprising placing each of the substances into a container, and inserting the container inside a pair of conductive rings of the sensor.

5. The capacitance-based moisture sensor calibration method of claim 2 further comprising inserting the container into a hollow plastic sleeve with the conductive rings attached to an outer surface of the sleeve.

* * * * *